US00PP17061P3

(12) United States Plant Patent
Boeder

(10) Patent No.: US PP17,061 P3
(45) Date of Patent: Aug. 29, 2006

(54) ***CHRYSANTHEMUM* PLANT NAMED 'CORHELLAS'**

(50) Latin Name: *Chrysanthemum morifolium*
Varietal Denomination: Corhellas

(75) Inventor: Mark Roland Boeder, The Hague (NL)

(73) Assignee: Chrysanthemum Breeders Association N.V., Aalsmeer (NL)

( * ) Notice: Subject to any disclaimer, the term of this patent is extended or adjusted under 35 U.S.C. 154(b) by 18 days.

(21) Appl. No.: 11/020,522

(22) Filed: Dec. 27, 2004

(65) Prior Publication Data

US 2006/0143758 P1 Jun. 29, 2006

(51) Int. Cl.
*A01H 5/00* (2006.01)

(52) U.S. Cl. ..... Plt./290

(58) Field of Classification Search ..... Plt./290
See application file for complete search history.

*Primary Examiner*—Anne Marie Grunberg
*Assistant Examiner*—Annette H Para
(74) *Attorney, Agent, or Firm*—Steptoe & Johnson LLP

(57) ABSTRACT

A *chrysanthemum* plant named 'Corhellas', characterized by its medium sized blooms with orange ray florets combined with a bronze center and prolific branching; natural season flower date September 20–27; blooming for a period of 5 weeks.

3 Drawing Sheets

BACKGROUND OF THE INVENTION

'Corhellas' is a product of a breeding and selection program for outdoor pot mums (garden mums) which had the objective of creating new *chrysanthemum* cultivars with a decorative type flower, a natural season flower date around September 20–27 (week 39), blooming for a period of 5 weeks. The new plant of the present invention comprises a new and distinct cultivar of *Chrysanthemum* plant. 'Corhellas' is a seedling resulting from a crossing program, which was set up by a previous breeder, and which records are unknown to the inventor. The new and distinct cultivar was discovered and selected as one flowering plant by Mark Roland Boeder on a cultivated field in Rijsenhout, The Netherlands in 2001. The first act of asexual production of 'Corhellas' was accomplished when vegetative cuttings were taken from the initial selection in 2001 in a controlled environment in Rijsenhout, The Netherlands, and propagated further at this location. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
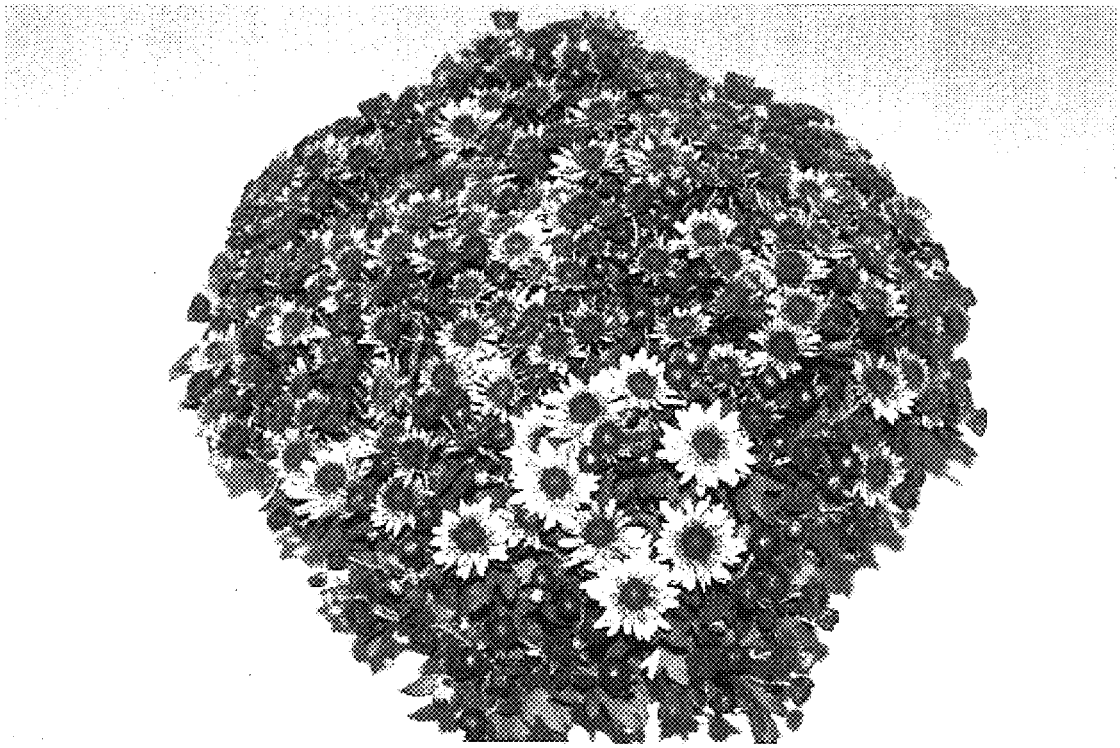
FIG. 1 shows a plant of the cultivar in full bloom.
Figure 2:
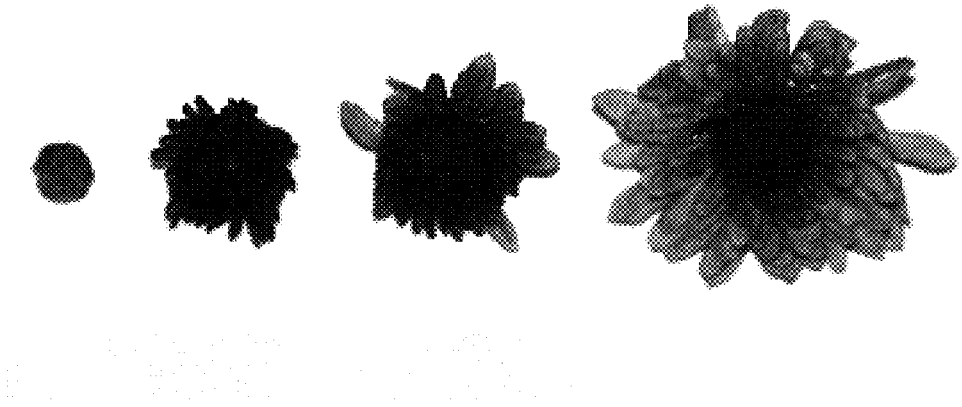
FIG. 2 shows the various stages of bloom of the new cultivar.
Figure 3:
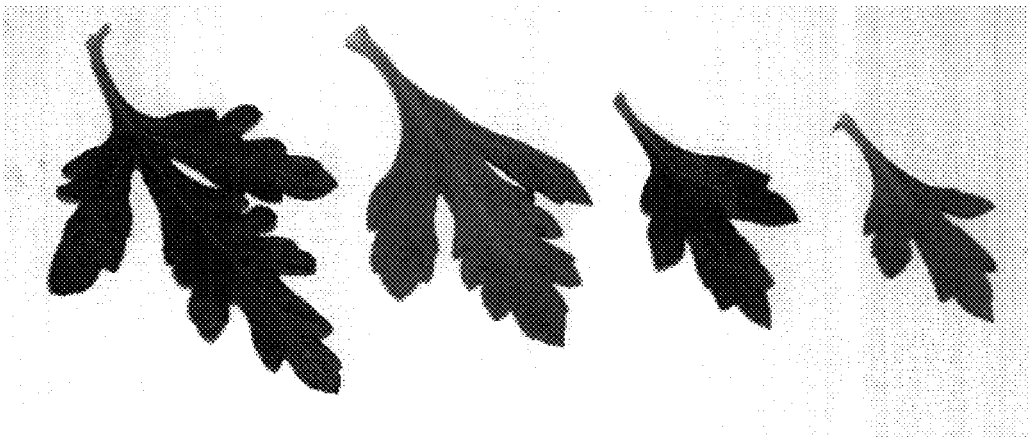
FIG. 3 shows the foliage of the new cultivar.

This new variety of *chrysanthemum* is of the botanical classification *Chrysanthemum morifolium* L. The observations and measurements were gathered from plants grown out door in Rijsenhout, The Netherlands under natural day length and temperature and planted in week 24 in 2004. The natural blooming date of this crop was September 20–27 (week 39). The average height of the plants was 25 cms. No growth retardants were used. No tests were done on disease or insect resistance or susceptibility. No tests were done on cold or drought tolerance. This new variety produces medium sized blooms with orange ray florets and a bronze center blooming for a period of 5 weeks.

From the cultivars known to inventor the most similar existing cultivars in comparison to 'Corhellas' are 'Iduna' (U.S. Plant Pat. No. 14,925) and 'Mars' (U.S. Plant Pat. No. 14,678). When 'Corhellas', 'Iduna' and 'Mars' are being compared the following similarities and differences are noticed: All three varieties have medium sized two tone blooms with a dark center. The differences of 'Corhellas' and 'Iduna' and 'Mars' is (1) Natural flowering date. (1) When planted in week 24, 'Iduna' and 'Mars' flower at a later date than 'Corhellas'.

The following is a description of the plant and characteristics that distinguish 'Corhellas' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

| Botanical Description of CULTIVAR 'CORHELLAS' | |
|---|---|
| Bud | |
| Size | Small; cross-section 0.5 cm, height 0.3 cm |
| Outside Color | Yellow-green 144D |
| Involucral bracts | 2 rows, length 7 mm, width 3 mm |
| Involucral bracts among disc-florets | Not present |
| Involucral bracts color | Green 138C |

TABLE 1-continued

| Botanical Description of CULTIVAR 'CORHELLAS' | |
|---|---|
| Bloom | |
| Type | Decorative |
| Height | 1 cm |
| Size | Medium |
| Fully Expanded | 4–5 cm |
| Peduncle length | 7 cm |
| Peduncle color | Green 143C–143D |
| Number of blooms per branch | Approx. 7 blooms per branch |
| Performance on the plant | 5 weeks |
| Seeds | Produced in small quantities, ovate grey-brown 199A, 1½ mm in length. |
| Fragrance | Typical *chrysanthemum,* slightly |
| Color | |
| Center of the flower | Immature Greyed-red 178A Mature Greyed-yellow 160A |
| Color of upper surface of the ray-florets | Yellow-orange 21B to Greyed-orange 163C |
| Color of the lower surface of the ray-florets | Greyed-orange 166C |
| Tonality from Distance | A garden mum with orange flowers and a bronze disc |
| Discoloration to color | Greyed-orange 163C |
| Ray florets | |
| Texture | Upper and under side smooth |
| Number | 160–180 |
| Cross-section | Flat |
| Longitudinal axis of majority | Straight |
| Length of corolla tube | 0.4 cm |
| Ray-floret margin | Entire |
| Ray-floret length | 2.2 cm |
| Ray-floret width | 0.4 cm |
| Ratio length/width | High |
| Shape of tip | Dentate |
| Disc florets | |
| Disc diameter | 0.5 cm |
| Distribution of disc florets | Few, only visible in mature stage |
| Shape | Tubular |
| Color | Yellow-green 154D |
| Receptacle shape | Conical raised |
| Reproductive Organs | |
| Stamen | Present in disc florets only |
| Stamen color | Yellow-green 144A |
| Pollen | Present |
| Pollen color | Yellow 7A |
| Styles | Thick |
| Style color | Yellow 13A |
| Style Length | 0.4 cm |
| Stigma color | Yellow-green 144A |
| Stigma Width | 1 mm |
| Ovaries | Enclosed in calyx |
| Plant | |
| Form | Grown as a spray type potmum, outdoor mounded and round |
| Growth habit | Spherical shape |
| Growth rate | Medium |
| Height | 25 cm |
| Width | 45 cm |
| Stem Color | Greyed-brown 199C with at base Greyed-Red 182C |

TABLE 1-continued

| Botanical Description of CULTIVAR 'CORHELLAS' | |
|---|---|
| Stem Strength | Strong |
| Stem Brittleness | Not brittle |
| Stem Anthocyanin Coloration | Present at base of stem |
| Internode lenght | 2.5–3 cm |
| Length of lateral branch | From top to bottom 17–19 cm |
| Lateral branch color | Green 138A–B |
| Lateral branch, attachment | Medium |
| Branching (average number of lateral branches) | Good with 8–10 breaks after pinching |
| Natural season blooming date | September 20–27 |
| Foilage | |
| Leaf color | Upper side Green 139A–139B Under side Green 138A–138B |
| Color midvein | Upper side Green 139D Under side Green 138D |
| Size | Medium; length 6–9 cm, width 4–6 cm |
| Quantity (number per lateral branch) | 13–15 |
| Shape | Ovate |
| Texture upper side | Glabrous |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Acute/obtuse |
| Apex | Mucronulate |
| Petiole lenght | 1–2 cm |
| Petiole color | Green 139D |

TABLE 2

| Differences with the Comparison varieties | | | |
|---|---|---|---|
| | 'Corhellas' | 'Iduna' | 'Mars' |
| Bloom size | 4–5 cm | 4.5–5 cm | 4.5–5 cm |
| Color center immature bloom | Greyed-red 178A | Greyed-red 179A | Greyed-red 179A |
| Color upper side ray-florets | Yellow-orange 21B to Greyed-orange 163C | Yellow-orange 22C | Yellow-orange 22B |
| Natural flowering date (when planted in week 24) | September 20–27 | October 4–11 | October 11–18 |

I claim:

1. A new and distinct variety of *chrysanthemum* plant as described and illustrated.

* * * * *